United States Patent [19]
Rucman et al.

[11] Patent Number: 5,288,724
[45] Date of Patent: Feb. 22, 1994

[54] ERGOLINE DERIVATIVES OF 2-PROPINYLAMINE, A PROCESS FOR THE MANUFACTURE THEREOF AND THE USE THEREOF FOR MEDICAMENTS

[75] Inventors: Rudolf Rucman; Breda Bole-Vunduk; Magdalena Ocvirk; Bogomila Lavric; Igor Krisch, all of Ljubljana, Slovenia

[73] Assignee: LEK, tovarna farmacevtskih, Slovenia

[21] Appl. No.: 901,983

[22] Filed: Jun. 22, 1992

[30] Foreign Application Priority Data

Jul. 1, 1991 [YU] Yugoslavia .................. 1154/91

[51] Int. Cl.$^5$ ............... A61K 31/44; C07D 457/00
[52] U.S. Cl. ............................ 514/288; 546/67; 546/69
[58] Field of Search .............. 546/67, 69; 514/288

[56] References Cited

U.S. PATENT DOCUMENTS 3,228,944  1/1966  Bernardi ................. 546/69
3,346,580 10/1967  Hofmann et al. ........ 546/69
4,064,249 12/1977  Mago ..................... 546/69

Primary Examiner—Marianne M. Cintins
Assistant Examiner—Catherine Scalzo
Attorney, Agent, or Firm—Pollock, Vande Sande & Priddy

[57] ABSTRACT

There are disclosed novel ergoline derivatives of 2-propinylamine of the general formula I wherein
$R_1$, $R_2$ and $R_3$ independently represent a hydrogen atom or a straight-chain or branched-chain $C_1$-$C_6$ alkyl group,
X represents a hydrogen or a halogen atom,
Z represents a carbonyl or methylene group and
$C_9$---$C_{10}$ represents a single or a double bond, diastereomeric forms, racemates and acid addition salts thereof.

There are also described a process for the manufacture of the compounds of the general formula I and a pharmaceutical composition containing the same.

The compounds of the general formula I can be used in the pharmaceutical industry as active substances for the manufacture of medicaments used in the treatment of hypertension, migraine, anxiety states, depressions, obesity etc.

16 Claims, No Drawings

ERGOLINE DERIVATIVES OF 2-PROPINYLAMINE, A PROCESS FOR THE MANUFACTURE THEREOF AND THE USE THEREOF FOR MEDICAMENTS

TECHNICAL FIELD OF THE INVENTION

The present invention belongs to the field of pharmaceutical industry and refers to novel ergoline derivatives of optionally substituted 2-propinylamine, which are useful in the pharmaceutical industry as active substances for the manufacture of medicaments used in the treatment of hypertension, migraine, anxiety states, depressions, obesity etc.

TECHNICAL PROBLEM

A constant need exists for novel, biologically highly active ergoline derivatives, which are suitable for use in human medicine.

PRIOR ART

Numerous ergoline compounds and processes for the manufacture thereof are known from published articles and patent literature, e.g. A. Stoll and A. Hoffmann, Helv. Chim. Acta 26, 922 (1943), W. L. Garbrecht, J. Org. Chem. 24, 368 (1959), and CH 469 735, CS 105 954, U.S. Pat. Nos. 3,141,887, and 2,736,728, respectively.

DESCRIPTION OF THE SOLUTION TO THE TECHNICAL PROBLEM

The present invention relates to novel ergoline derivatives of optionally substituted 2-propinylamine of the general formula I

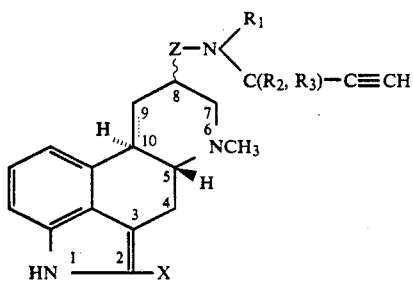

wherein
$R_1$, $R_2$ and $R_3$ independently represent a hydrogen atom or a straight-chain or branched-chain $C_1$-$C_6$ alkyl group,
X represents a hydrogen or a halogen atom,
Z represents a carbonyl or methylene group and
$C_9\text{---}C_{10}$ represents a single or a double bond,
and to the acid addition salts thereof.

Since the compounds of the general formula I contain a chiral centre on the 8-position, they can exist in the form of diastereoisomers having $8\alpha$- or $8\beta$-configuration or in the form of a mixture of both diastereoisomers. The invention encompasses both pure diastereoisomers as well as mixtures thereof and racemates.

The pharmaceutically acceptable acid addition salts of the compound of the general formula I are prepared with physiologically acceptable organic or inorganic acids such as acetic, formic, maleic, tartaric, citric, methanesulfonic, hydrobromic, hydrochlorid, sulphuric acids etc.

Novel ergoline derivatives of 2-propinylamine of the general formula I can be prepared in accordance with known methods described in the literature; however, the process of the present invention is preferable and gives the best results.

According to the invention, the compounds of the general formula I are prepared by condensing a compound of formula II

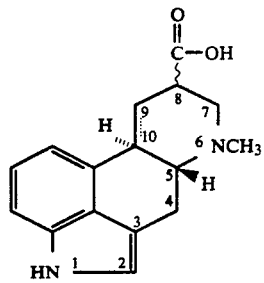

wherein the bond between the $C_9$ and $C_{10}$ is a single or a double one, with an N-substituted 2-propinylamine of the general formula III

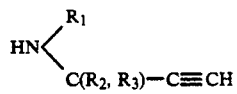

wherein the substituents are as defined hereinbefore, to a compound of the general formula IV

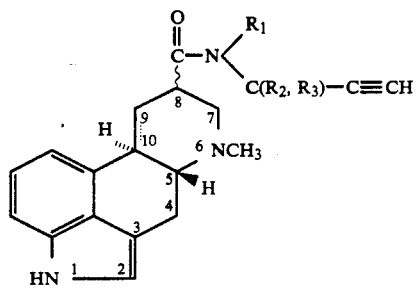

wherein $R_1$, $R_2$, $R_3$ and $C_9\text{---}C_{10}$ are as defined hereinbefore, which is isolated, purified and selectively halogenated at the 2-position.

Optionally, a compound of the general formula I, wherein Z represents a carbonyl group and wherein $R_1$, $R_2$, $R_3$ and $C_9\text{---}C_{10}$ are as defined hereinbefore, can be reduced to a corresponding compound of the general formula I, wherein Z represents a methylene group, which compound is selectively brominated at the 2-position.

The condensation of the compound of the formula II with a compound of the general formula III is carried out in an inert organic solvent such as dimethylformamide, in the presence of a condensing agent such as diphenylphosphorylazide (DPPA), and of an organic base such as triethylamine.

The selective halogenation of a compound of the general formula IV is carried out by means of mild halogenating agents such as N-bromosuccinimide, pyrrolidone-(2)-hydrotribromide, N-chloro-2,6-dichloro-4-nitroacetanilide or 3-bromo-6-chloro-2-methylimidazo(1,2-b)piridazine dibromide, in an inert organic solvent such as dioxane or methylene chloride or in a mixture of organic solvents. Methods can be used that were described by R. Ručman, J. Koršič and M.

Jurgec, Il Farmaco, Ed. Sci. 38, 406 (1983) and in CH 263 279.

The reduction of a compound of the general formula I, wherein Z represents a carbonyl group, to a compound of the general formula I, wherein Z represents a methylene group, is carried out by means of well-known reducing agents such as sodium aluminium bis-(2-methoxyethoxy)dihydride, in an inert organic solvent such as toluene, at temperatures between room temperature and 100° C., preferably at about 60° C.

The inventive compounds of the general formula I are biologically highly active. Their effects were demonstrated in pharmacological tests and binding studies in different receptor models as shown hereinafter.

The compounds of the general formula I can be used as medicaments in the form of pharmaceutical compositions containing these compounds, optionally together with acceptable pharmaceutical carriers. The compounds can be used as medicaments e.g. in the form of pharmaceutical compositions containing these compounds in mixtures with organic or inorganic pharmaceutical carriers suitable for enteral or parenteral application such as water, gum arabic, gelatine, lactose, starch, magnesium stearate, talc, vegetable oils, polyglycols etc., and various other auxiliary substances. The dosage unit of the composition contains from 0.001 to 10 mg of the compound of the invention.

The daily dose is from 0.0001 to 0.1 mg of the active substance per kg of body weight.

Another aspect of the invention is the use of the inventive compounds in the manufacture of medicaments that can be used in the treatment and prevention of diseases such as hypertension, migraine, anxiety states, depressions, obesity etc.

A further object of the invention are medicaments containing one of the compounds of the invention of the general formula I and/or physiologically acceptable acid addition salts thereof.

The invention is illustrated by the following Examples.

EXAMPLE 1

9,10-Didehydro-N-(2'-propinyl)-6-methylergoline-8β-carboxamide

D-lysergic acid (30 g, 0.112 moles) was suspended in dry dimethylformamide (DMF) (600 ml). 2-Propinylamine (15 ml, 0.2187 moles) and diphenylphosphorylazide (DPPA) (36 ml, 0.1668 moles) were added thereto, the mixture was stirred at room temperature for 10 minutes, which was followed by a slow addition of dry triethylamine (24 ml, 0.172 moles) and stirring for another 2 hours at room temperature.

The reaction mixture was then evaporated in vacuo to a thick gum, which was dissolved in methylene chloride (600 ml). The resulting solution was shaken with a 2% ammonia solution (2×600 ml). The organic phase was separated, dried over sodium sulfate and the solvent was evaporated in vacuo. The obtained dry title compound (49.3 g) was purified by chromatography over a column (7×36 cm) packed with basic aluminium oxyde (1800 g; Merck Geduran 90, activity II.-III.).

Fractions 20 to 30 yielded 14.53 g of the compound, which did not crystalize as the free base but did as the tartrate from ethanol. Thus, there were obtained 14.6 g (28.8%) of the title compound in the form of tartrate, m.p. 148°-150° C. Specific rotation $[\alpha]_D^{20} = -66.4°$ (c=1, CHCl$_3$)

EXAMPLE 2

2-Bromo-9,10-didehydro-N-(2'-propinyl)-6-methylergoline-8β-carboxamide

The compound obtained in Example 1 (4.9 g, 0.016 moles) was dissolved in a mixture of methylene chloride and dioxan (85:15; 400 ml). Finely ground pyrrolidone-(2)-hydrobromide (5 g, corresponding to 0.024 moles of Br$_2$) was added all at once under stirring and the mixture was stirred for 40 minutes. The reaction was stopped by the addition of ammonia, the mixture was filtered and the filtrate was washed with sodium bicarbonate (2×600 ml of a 2% solution). The methylene chloride solution was evaporated to dryness and the crude substance (3.82 g) was purified by chromatography over a column (4×15 cm) packed with silica gel (Merck 60, 0.063-0.200 mm, 92 g). Elution was carried out with a mixture of methylene chloride and acetone (80:20). Fractions 17 to 26 (of 50 ml each) were evaporated and the dry residue (1.01 g) was crystallized as oxalate from methanol/ether. The title compound was obtained in the form of oxalate (1.18 g), m.p. 169°-173° C. Yield: 15.5% of the theory.

Specific rotation $[\alpha]_D^{20} = -78.2°$ (c=0.5, CHCl$_3$)

EXAMPLE 3

9,10-Didehydro-N-methyl-N-(1',1'-diethyl-2'-propinyl)-6-methylergoline-8α-carboxamide According to the procedure as described in Example 1, D-lysergic acid was reacted with N-methyl-N-(1',1'-diethyl-2'-propinyl)amine. The yield of the title compound was 24.4% of the theory, m.p. 143°-148° C.

Specific rotation $[\alpha]_D^{20} = +342°$ (c=0.5, CH$_3$OH)

EXAMPLE 4

9,10-Didehydro-N-methyl-N-(2'-propinyl)-6-methylergoline-8β-carboxamide

According to the procedure as described in Example 1, D-lysergic acid was reacted with N-methyl-N-(2'-propinyl)amine. The title compound was crystallized as tartrate from methanol. Yield: 34.6% of the theory, m.p. 140°-144° C.

Specific rotation $[\alpha]_D^{20} = +30.1°$ (c=1, CH$_3$OH)

EXAMPLE 5

2-Bromo-9,10-didehydro-N-methyl-N-(2'-propinyl)-6-methylergoline-8β-carboxamide

According to the procedure as described in Example 2, 9,10-didehydro-N-methyl-N-(2'-propinyl)-6-methylergoline-8β-carboxamide was brominated. The title compound was crystallized from ethanol. Yield: 42.9% of the theory, m.p. 119°-123° C.

Specific rotation $[\alpha]_D^{20} = +30.1°$ (c=1, CH$_3$OH)

EXAMPLE 6

N-Methyl-N-(2'-propinyl)-6-methylergoline-8β-carboxamide 9,10-Dihydrolysergic acid (8.0 g, 0.0296 moles, dried in vacuo at 120° C.) and N-methyl-N-(2'-propinyl)amine (4.01 g, 0.058 moles) were suspended in DMF (200 ml, dried with 3×10$^{-4}$ μm molecular sieves). DPPA (4 ml, 0.0436 moles) was added thereto under stirring, which was continued for another 15 minutes, and triethylamine (6.4 g, 0.046 moles, dried over NaOH and then distilled) was added thereto. The reaction mixture was stirred at room temperature for 6 hours. The unreacted 9,10-dihydrolysergic acid (1.33 g=16.6%) was filtered off as a white solid. The filtrate was evaporated in vacuo to a thick gum, which was dissolved in a mixture of ethyl acetate and methylene chloride (1:1, 300 ml) and washed with a 2% ammonia solution (3×300 ml). The organic phase was dried over $Na_{32}SO_4$, purified with activated charcoal and concentrated in vacuo to a small volume. The white solid, which crystallized, was filtered off and recrystallized from dimethyl sulphoxide by addition of water. The yield of the title compound was 7.54 g (79.25% of the theory), m.p. 194°-196° C.

Specific rotation $[\alpha]_D^{20} = +71.0°$ (c=0.5, $CHCl_3$)

EXAMPLE 7

2-Bromo-N-methyl-N-(2'-propinyl)-6-methylergoline-8β-carboxamide 9,10-Dihydrolysergic acid N-methyl-N-(2'-propinyl)amide (0.64 g, 2 mmoles) was dissolved in a nitrogen atmosphere in a mixture of methylene chloride and dioxan (80:20, 20 ml), and pyrrolidone-(2)-hydrotribromide (1.22 g, 3 mmoles) in $CHCl_2$ (220 ml) was added thereto. The reaction mixture was stirred for 20 minutes. The solution was then washed with a 2% aqueous ammonia solution (3×300 ml). The organic phase was dried over $Na_2SO_4$ and the solvent was evaporated in vacuo. The obtained brown residue (1.21 g) was purified by chromatography over a column (2×30 cm) packed with silica gel (Merck 60, 0.040 to 0.063 mm, 60 g). The elution was carried out with a mixture of methylene chloride and acetone (8:2). Fractions containing the title compound were evaporated in vacuo. The obtained residue (0.85 g) was crystallized from boiling ethyl acetate. The obtained white title compound (0.67 g, 83.7% of the theory) had a m.p. of 239°-243° C.

Specific rotation $[\alpha]_D^{20} = -100.8°$ (c=1, $CH_2Cl_2/CH_3OH = 1:1$)

EXAMPLE 8

8β-Methyl-N-methyl-N-(2'-propinyl)-6-methylergoline

D-Lysergic acid N-methyl-N-(2'-propinyl) amide (7.51 g, 0.0235 moles) was dissolved in anhydrous toluene (900 ml) at 60° C. To the solution, sodium aluminium bis(2-methoxyethoxy)-dihydride (38.38 g, a 70% solution in benzene) was gradually added under stirring at 60°-70° C. and the stirring was continued for another hour. The mixture was cooled, ethanol (96%, 20 ml) and a 2% aqueous solution of sodium hydroxyde (200 ml) were added, and the layers were separated. The organic phase was extracted with a 2% aqueous solution of sodium hydroxyde (2×500 ml), dried over $Na_2SO_4$ and evaporated to dryness in vacuo. The residue was dissolved in methylene chloride and the solvent was partly evaporated; the crude product that crystallized was recrystallized from a mixture of ethyl acetate and methylene chloride (1:1) while the solvent was slowly evaporated in vacuo. The title compound (4.04 g, 56.28% of the theory) had a m.p. of 203°-205° C. (with decomposition).

Specific rotation $[\alpha]_D^{20} = +59.5°$ (c=1, $CHCl_3$)

EXAMPLE 9

2-Bromo-8β-methyl-N-methyl-N-(2'-propinyl)-6-methylergoline

N-methyl-N-(2'-propinyl)-lysergamine (1.65 g, 5.4 mmoles) was dissolved in a mixture of methylene chloride and dioxan (85:15, 20 ml). Pyrrolidone-(2)-hydrotribromide (6.6 g, corresponding to 12 mmoles of $Br_2$) was added thereto under stirring at 10° C. and the stirring was continued for 1 hour. The reaction mixture was filtered, the insoluble was washed with the above mixture of methylene chloride and dioxan (85:15, 100 ml) and the combined filtrates were washed with a saturated solution of sodium bicarbonate (2×100 ml). The organic phase was dried over $Na_2SO_4$ and evaporated to dryness. The obtained dry residue (1.70 g) was dissolved in a mixture of methylene chloride and ethyl acetate (1:1) and purified by chromatography over a column (3×20 cm) packed with silica gel (Merck 60, 0.2 to 0.063 mm, 64.6 g). The title compound was eluted with pure ethyl acetate. The appropriate fractions were evaporated to dryness in vacuo and dissolved in a mixture of ethyl acetate and methylene chloride (1:1). Following a partial evaporation of the solvent and standing overnight at −15° C., the title compound (0.67 g, 32.28% of the theory) was crystallized in the form of white crystals, m.p. 208°-212° C.

Specific rotation $[\alpha]_D^{20} = +22.8°$ (c=0.5, $CH_3OH$)

Pharmacological Tests 9,10-Didehydro-N-(2'-propinyl)-6-methylergoline-8β-carboxamide (compound of Example 1)

The compound caused a constriction of the isolated rabbit thoraric aorta. The intrinsic activity was comparable to that of serotonin. At a concentrationof 1 μM the vasoconstriction was the result of the activation of $\alpha_1$-adrenergic receptors.

On the isolated rat uterus (the method was described by De Jalon et. al., Pharmacoter. act. 3, 313 (1945), hereinafter "Jalon"), it inhibited serotonin (2.47×10⁻⁸M)induced contractions ($IC_{50} = 5.37 \times 10^{-8}$M).

The compound had no uterotonic activity (isolated rat uterus, see Jalon).

Approximately 2 minutes after an intravenous application of the compound (450 μg/kg) to pentobarbital-anesthetized normotensive rats, a strong reduction in the carotid artery pressure and heart rate set in, followed by exitus.

The intravenous application of the compound in a dose of 450 μg/kg to pithed rats in accordance with the method described by Gillespie et al., Br. J. Pharmacol. 40, 257-267 (1970) (hereinafter "Gillespie") caused a transient, yet very strong peripheral vasoconstriction.

In a dose of 4 mg/kg i.p. the compound inhibited the head twitch response after the injection of D,L-5-hydroxytryptophan/carbidopa (DL-5 HTP/carbidopa) by 62%. The substance was injected 15 minutes prior to DL-5-HTP. The head twitch was recorded from 30 to 35 minutes after the DL-5-HTP injection (modified method according to Handley and Singh, Br. J. Pharmacol. 86, 297 (1985)).

After an i.p. application of the substance in a dose of 5 mg/kg to mice, a very strong dilatation of the pupil occurred (the method was described by Pulewka in Archiv f. Experiment. Path. u. Pharmakol. 168, 37 (1932), hereinafter "Pulewka"). The mice became agitated, piloerection, tremor and excitation took place. After 60 minutes the effect was quickly reduced.

The binding studies showed that the compound possessed affinity to

[³H] 8-OH-DPAT binding site (5-HT$_{1A}$ serotoninergic receptor); a further functional test indicated an agonistic activity;

[³H] DTG binding site (sigma receptor); a further functional test indicated an antagonistic activity.
Note:
8-OH-DPAT = 8-hydroxy-2-(di-n-propylamino)-tetraline
DTG = 1,3-di-o-toluylguanidine 2-Bromo-9,10-didehydro-N-(2'-propinyl)-6-methylergoline-8β-carboxamide (compound of Example 2)

On the isolated rabbit thorarcic aorta the compound competitively inhibited the constrictive effect of serotonin ($pA_2 = 8.13$).

On the isolated rat uterus (see Jalon) it inhibited the serotonin-induced contractions ($IC_{50} = 2.69 \times 10^{-8}$M).

At a concentration of 1000 ng/ml it caused a 100% blocking of spontaneous uterus contractions in rats (see Jalon).

The maximum reduction in carotid artery pressure (by 15%) and in heart rate (by 5%) with respect to initial levels set in immediately after the application of the compound (450 μg/kg, i.v.) to pentobarbital-anesthetized normotensive rats. The effect was of a transient nature (up to 20 minutes).

The i.p. application of the compound in a dose of 450 μg/kg to pithed rats (see Gillespie) caused a sustained mean increase of the diastolic pressure by 20% with respect to the control.

The i.p. application of the compound in a dose of 5 mg/kg to mice caused a marked dilatation of the pupil (see Pulewka).

The binding studies showed that the compound possessed affinity to
[³H] 8-OH-DPAT binding site (5-HT$_{1A}$ serotoninergic receptor); a further functional test did not indicate any activity;
[³H] DTG binding site (sigma receptor); a further functional test indicated an antagonistic activity.

9,10-Didehydro-N-methyl-N-(2'-propinyl)-6-methylergoline-8β-carboxamide (compound of Example 4)

The compound caused a constriction of the isolated rabbit thoracic aorta ($pD_2 = 6.41$). The intrinsic activity was comparable to that of serotonin. At a concentration of 0.39 μM ($EC_{50}$) it caused vasoconstriction, which was predominantly the result of the activation of $\alpha_1$-adrenergic receptors and to a lesser extent of the activation of 5-HT$_2$ receptors. At a preparation with inactivated $\alpha_1$-adrenergic receptors, the compound (0.01 to 0.3 μM) showed a serotonin-antagonistic activity. At smaller doses (0.1 μM) the antagonism was of competitive nature ($pA_2 = 8.37$), whereas at higher doses there was a noticeable decrease of the maximum activity of serotonin.

At a concentration of $3.20 \times 10^{-8}$M it showed a uterotonic activity (see Jalon), which was lesser than the one of methylergometrine maleate ($5.49 \times 10^{-9}$ to $10.98 \times 10^{-9}$M).

When applied to pentobarbital-anesthetized normotensive rats (450 μg/kg, i.v.), the compound caused statistically non-significant changes in carotid artery pressure and a mean 20% decrease in the heart rate with respect to the initial level (respiratory troubles could be perceived).

An i.v. application of the compound (450 μg/kg) to pithed rats (see Gillespie) caused a transient, yet extraordinarily strong peripheric vasoconstriction.

The compound (0.125 to 4 mg/kg, i.p.) caused a head twitch response in mice. The maximum activity took place at a dose of 1 mg/kg i.p., at higher doses the activity decreased (autoinhibitory effect).

The compound caused a dose-dependent dilatation of the pupil in mice (see Pulewka), an increased activity, tremor and piloerection.

The acute toxicity in mice after intravenous application was $LD_{50} = 55$ (47–63) mg/kg, determined in accordance with the method described by Miller and Tainter, Proc. Soc. Exptl. Biol. Med. 57, 261 (1944).

2-Bromo-9,10-didehydro-N-methyl-N-(2'-propinyl)-6-methylergoline-8β-carboxamide (compound of Example 5)

On the isolated rabbit thoracic aorta the compound competitively inhibited the constrictive activity of serotonin ($pA_2 = 7.93$) and noradrenaline ($pA_2 = 6.45$).

On the isolated rat uterus (see Jalon) it inhibited serotonin ($2.47 \times 10^{-8}$M)-induced contractions ($IC_{50} = 1.25 \times 10^{-8}$M). It had no uterotonic activity (see Jalon).

An intravenous application of the compound in a dose of 450 μg/kg to pentobarbitalanesthetized normotensive rats caused a small, yet statistically significant decrease in carotid artery pressure and heart rate. The maximum effect set in immediately after the application of the compound (a 10% decrease with respect to the initial level), decreasing gradually with time.

An intravenous application of the compound (450 μg/kg) to pithed rats (see Gillespie) caused a slowly developing peripheric vasoconstriction (a 20% increase with respect to the control).

The compound ($ID_{50} = 3.8$ mg/kg, i.p.) inhibited the head twitch response in mice after the injection of L-5 HTP/carbidopa. The compound was injected 15 minutes prior to L-5-HTP (modified method according to Handley and Singh, Br. J. Pharmacol. 86, 297 (1985)).

The binding studies showed that the compound possessed affinity to
[³H] 8-OH-DPAT binding site (5-HT$_{1A}$ serotoninergic receptor); a further functional test did not indicate any activity;
[³H] DTG binding site (sigma receptor); a further functional test indicated an antagonistic activity.

8β-Methyl-N-methyl-N-(2'-propinyl)-6-methylergoline (compound of Example 8)

On the isolated rabbit thoracic aorta the compound competitively inhibited the constrictive activity of serotonin ($pA_2 = 9.13$) and noradrenaline ($pA_2 = 6.39$).

On the isolated rat uterus (see Jalon) it strongly inhibited serotonin ($2.47 \times 10^{-8}$M)induced contractions ($IC_{50} = 1.85 \times 10^{-9}$M).

It had no uterotonic activity (see Jalon).

On the isolated rabbit vena cava inferior the compound caused a minimal venous constriction ($1 \times 10^{-7}$M). On the isolated rabbit vena cava it inhibited the activity of noradrenaline on venous constrictions ($pA_2 = 6.63$).

An intravenous application of the compound in a dose of 450 μg/kg to pentobarbitalanesthetized normotensive rats caused a strong and sustained decrease in carotid artery pressure (by 20%) and in heart rate (by less than 20%) with respect to the initial level.

An intravenous application of the compound (450 μg/kg) to pitched rats (see Gilespie) caused a sustained mean increase in diastolic pressure by 20% with respect to the control level.

In urethane-anestetized normotensive rats the compound (450 μg/kg, i.v.) intensified the adrenaline (10 μg/kg, i.v.)-induced vasopressoric response.

After an i.p. application (5 mg/kg) the compound caused a strong dilatation of the pupil in mice (see Pulewka).

The binding studies showed that the compound possessed affinity to

[$^3$H]8-OH-DPAT binding site (5-HT$_{1A}$ serotoninergic receptor); a further functional test did not indicate any activity;

[$^3$H] DTG binding site (sigma receptor); a further functional test indicated an antagonistic activity;

[$^3$H] pirenzepine binding site (M$_1$ muscarinic receptor); a further functional test indicated an antagonistic activity.

We claim:

1. Ergoline derivatives of 2-propinylamine of the general formula I

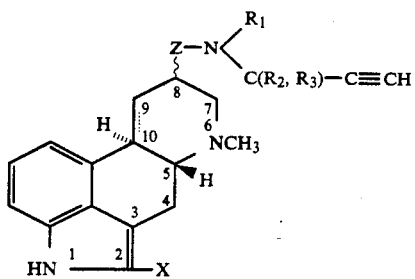

wherein
R$_1$, R$_2$ and R$_3$ independently represent a hydrogen atom or a straight-chain or branched-chain C$_1$–C$_6$ alkyl group,
X represents a hydrogen or a halogen atom,
Z represents a carbonyl or methylene group and
C$_9$–C$_{10}$ represents a single or a double bond, diastereomeric forms, racemates and acid addition salts thereof.

2. Derivative of claim 1 which is 9,10-Didehydro-N-(2′-propinyl)-6-methylergoline-8β-carboxamide.

3. Derivative of claim 1 which is 2-Bromo-9,10-didehydro-N-(2′-propinyl)-6-methylergoline-8β-carboxamide.

4. Derivative of claim 1 which is 9,10-Didehydro-N-methyl-N-(2′-propinyl)-6-methylergoline-8β-carboxamide.

5. Derivative of claim 1 which is 2-Bromo-9,10-didehydro-N-methyl-N-(2′-propinyl)-6-methylergoline-8β-carboxamide.

6. Derivative of claim 1 which is 8β-Methyl-N-methyl-N-(2′-propinyl)-6-methylergoline.

7. A pharmaceutical composition comprising an antidepressant effective amount of a compound of claim 1 or an acid addition salt thereof, together with pharmaceutically acceptable carriers.

8. A pharmaceutical composition comprising an anxiolytic effective amount of a compound of claim 1 or an acid addition salt thereof, together with pharmaceutically acceptable carriers.

9. The pharmaceutical composition of claim 7 which contains a therapeutically effective amount of 2-Bromo-9,10-didehydro-N-methyl-N-(2′-propinyl)-6-methylergoline-8β-carboxamide, or acid addition salt thereof.

10. The pharmaceutical composition of claim 7 which contain a therapeutically effective amount of 8β-Methyl-N-methyl-N-(2′-propinyl)-6-methylergoline, or acid addition salt thereof.

11. A method of treating depression in a patient in a need of such treatment comprising administering to said patient, a therapeutically effective amount of an ergolinyl compound of claim 1.

12. A method of treating anxiety in a patient in a need of such treatment comprising administering to said patient, a therapeutically effective amount of an ergolinyl compound of claim 1.

13. The method of claim 11 wherein said compound is 2-Bromo-9,10-didehydro-N-methyl-N-(2′-propinyl)-6-methylergoline-8β-carboxamide, or acid addition salt thereof.

14. The method of claim 11 wherein said compound is 8β-Methyl-N-methyl-N-(2′-propinyl)-6-methylergoline, or acid addition salt thereof.

15. The method of claim 12 wherein said compound is 2-Bromo-9,10-didehydro-N-methyl-N-(2′-propinyl)-6-methylergoline-8β-carboxamide, or acid addition salt thereof.

16. The method of claim 12 wherein said compound is 8β-Methyl-N-methyl-N-(2′-propinyl)-6-methylergoline, or acid addition salt thereof.

* * * * *

UNITED STATES PATENT AND TRADEMARK OFFICE
CERTIFICATE OF CORRECTION

PATENT NO. : 5,288,724
DATED : February 22, 1994
INVENTOR(S) : Rucman et al.

It is certified that error appears in the above-identified patent and that said Letters Patent is hereby corrected as shown below:

```
On title page,
At Section [73], please change the Assignee from "LEK,
tovarna farmacevtskih, Slovenia" to ---LEK,
tovarna farmacevtskih in kemicnih izdelkov, d.d.,
Ljubljana, Slovenia---.
```

Signed and Sealed this

Twenty-fifth Day of February, 1997

Attest:

BRUCE LEHMAN

*Attesting Officer*  *Commissioner of Patents and Trademarks*